United States Patent [19]
Riley et al.

[11] Patent Number: 5,463,142
[45] Date of Patent: Oct. 31, 1995

[54] METHOD FOR THE PREPARATION OF D-CHIRO-INOSITOL

[75] Inventors: David A. Riley, Kenosha, Wis.; Steven A. Chamberlin, Waukegan; Ashok V. Bhatia, Libertyville, both of Ill.

[73] Assignee: Abbott Laboratories, Abbott Park, Ill.

[21] Appl. No.: 337,656

[22] Filed: Nov. 10, 1994

[51] Int. Cl.$^6$ .................................................. C07C 35/16
[52] U.S. Cl. ........................... 568/833; 568/822; 568/832
[58] Field of Search ................................ 568/822, 832, 568/833

[56] References Cited

U.S. PATENT DOCUMENTS

| | | | |
|---|---|---|---|
| 5,091,596 | 2/1992 | Kennington et al. | 568/333 |
| 5,260,472 | 11/1993 | Chen | 568/161 |
| 5,406,005 | 4/1995 | Piccariello | 568/833 |

FOREIGN PATENT DOCUMENTS 652647  1/1993  Australia ................................ 568/833

*Primary Examiner*—Werren B. Lone
*Attorney, Agent, or Firm*—Andreas M. Danckers; Brian R. Woodworth

[57] ABSTRACT

A method for the preparation of D-chiro-inositol from kasugamycin, comprising the steps of:

(a) reacting kasugamycin with an acetylating agent to form a crude hexa-acetate intermediate;
(b) purifying the crude intermediate to form purified hexa-acetate intermediate;
(c) deacetylating the purified intermediate to form D-chiro-inositol; and
(d) isolating the D-chiro-inositol.

The method permits efficient, large-scale preparation of D-chiro-inositol without the need for extensive chromatographic purification of the final D-chiro-inositol product.

27 Claims, No Drawings

METHOD FOR THE PREPARATION OF D-CHIRO-INOSITOL

BACKGROUND OF THE INVENTION

D-chiro-inositol and myo-inositol, which have respectively the structural formulae

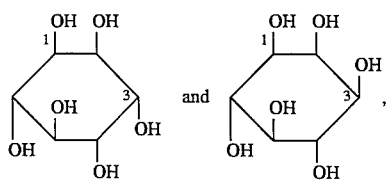

occur naturally, with the more abundant myo-isomer being generally found in plants as its hexaphosphate, phytic acid, or as salts of the hexaphosphate, phytin. In mammals, the mono- and polyphosphate forms of these compounds are components of cellular membranes and can function as insulin mediators. Following the observation that the conversion of myo- to chiro-inositol is deficient in mammals suffering from certain types of diabetes, it has been proposed more recently that supplementing the diet with D-chiro-inositol can help control blood glucose levels of patients affected by this disease.

The need for investigational and commercial quantifies of D-chiro-inositol has led to the development of several methods for the isolation (by extraction from plant tissues), partial synthesis or complete synthesis of that compound. Especially promising is hydrolysis of the aminoglycoside kasugamycin (produced by fermentation of *Streptomyces kasugaspinus*) as described in U.S. Pat. No. 5,091,596 issued to Kennington et al. According to that patent, kasugamycin is treated with trifluoroacetic acid for 3 hours at 100° C., after which the resulting D-chiro-inositol is isolated by resin and gel chromatography and purified by recrystallization from 90% ethanol. Alternatively, kasugamycin may be treated with hydrochloric acid for 8 hours at 90° C., followed by isolation of the D-chiro-inositol by resin chromatography and subsequent purification.

However, when preparing larger amounts of product, a relative drawback of each of the above acid hydrolysis procedures is the expense of the chromatographic isolation step in which D-chiro-inositol is purified. Similarly, the isolation of D-chiro-inositol product from dilute aqueous solution, as by lyophilization, may be unduly time-consuming when carded out as a part of an industrial process. Consequently, there remains a need for more efficient methods whereby high-purity D-chiro-inositol can be prepared, economically and on a large scale, from kasugamycin.

SUMMARY OF THE INVENTION

It has now been found that D-chiro-inositol can be obtained from kasugamycin by a substantially more efficient route, namely, by acetolysis of the aminoglycoside to form the intermediate hexa-O-acetyl-D-chiro-inositol ("hexa-acetate"). This hexa-acetate is readily isolated and purified before deacetylation of the intermediate. Moreover, deacetylation of the hexa-acetate intermediate may be carded out under conditions which allow immediate crystallization of D-chiro-inositol in significantly pure form, eliminating the need for extensive purification of the final product. Overall, the semi-synthesis of the present invention produces D-chiro-inositol of satisfactory purity without chromatographic purification and, therefore, with a savings of time and expense when compared to previously-described methods.

Accordingly, the present invention comprises a method for the preparation of D-chiro-inositol from kasugamycin, comprising the steps of:

(a) reacting kasugamycin with an acetylating agent to form crude hexa-acetate;

(b) purifying the crude hexa-acetate to form purified hexa-acetate;

(c) deacetylating the purified hexa-acetate to form D-chiro-inositol; and (d) isolating the D-chiro-inositol.

The D-chiro-inositol isolated in the fourth step above may optionally be subjected to an additional step, in which the D-chiro-inositol is further purified by re-crystallization.

Moreover, the second (purification) step may comprise a number of particular sub-steps, namely:

(i) substantially removing the acetylating agent to form a residue;

(ii) diluting the residue in a suitable solvent system to form a solution of crude hexa-acetate;

(iii) filtering the solution of crude hexa-acetate to form a solution of purified hexa-acetate; and (iv) substantially removing the solvent.

An additional sub-step may optionally be included, between sub-steps (ii) and (iii), wherein the solution of crude hexa-acetate is neutralized before filtration. Alternatively, the optional neutralization sub-step may take place between sub-steps (iii) and (iv), that is, after filtration.

DETAILED DESCRIPTION OF THE INVENTION

In the method of the present invention as summarized above, kasugamycin is reacted, preferably in the presence of an acid catalyst, with an acetylating agent under conditions which favor acetolysis of the aminoglycoside. Ideally, the kasugamycin is in the form of an hydrochloride salt; however, the term "kasugamycin" refers to both kasugamycin base as well as any acid- or base-addition salt which is readily available and suitable for use as described herein.

In a favored embodiment of the invention, the acetylating agent is chosen from among acetic anhydride, a mixture of acetic anhydride and acetic acid, trifluoroacetic anhydride, a mixture of trifluoroacetic anhydride and trifluoroacetic acid, and a mixture of acetyl halide and acetic acid; preferred is a mixture of acetic anhydride and acetic acid in a ratio (by volume) of about 1:1. The acid catalyst, on the other hand, may be chosen from among mineral acids and Lewis acids. Suitable mineral acids include hydrochloric acid, hydrobromic acid, hydrofluoric acid, nitric acid, sulfuric acid, and perchloric acid; suitable Lewis acids include $BF_3$-etherate and $FeCl_3$. Especially preferred acid catalysts include concentrated sulfuric acid and 70% perchloric acid, of which 10 drops suffice per 100 mL total reaction volume. The acetolysis reaction may be carded out for a period of time which depends on temperature and the choice of reagents; the time required can range from two hours to three days, and the temperature may vary from ambient to 120° C.

The product of the acetolysis reaction is hexa-O-acetyl-D-chiro-inositol or, in the event that trifluoroacetic anhydride is used as acetylating agent, hexa-O-trifluoroacetyl-D-chiro-inositol. It is intended, in both the specification and the claims hereof, that the term "hexa-acetate" encompasses both the hexa-O-acetyl and the hexa-O-trifluoroacetyl intermediates.

Following acetolysis, the crude hexa-acetate may be purified as described above beginning with removal of the acetylating agent, preferably by vacuum evaporation as in a rotary evaporator, typically resulting in the formation of an oily residue. Once "stripped" of substantially all of the acetylating agent, the residue may then be diluted in a solvent system which ideally comprises a first, polar solvent chosen from among ethyl acetate, $CH_3CN$, $CH_2Cl_2$, $CHCl_3$, and 1,2-dichloroethane. This solvent system may optionally also comprise a second, non-polar solvent chosen from among long-chain hydrocarbons and aromatic hydrocarbons, especially pentane, hexane, heptane, benzene, xylene or toluene. Preferred is a system comprising ethyl acetate and hexane in a ratio (by volume) of about 1:1.

According to one embodiment of the invention, the resulting solution of crude hexa-acetate is then passed through a filter material which retains any solids as well as some of the contaminant by-products of the acetolysis reaction. Depending on the choice of solvent systems, suitable filter materials may include silica gel, alumina, activated carbon, diatomaceous earth, and a mixture of alumina and diatomaceous earth; preferred for use with the above ethyl acetate/hexane system is silica gel. Residual acids in the solution of purified hexa-acetate may then be neutralized, in particular by washing the solution with an aqueous solution of sodium bicarbonate. (Alternatively, the neutralization step may be carried out before purification, as by washing the crude hexa-acetate solution prior to filtering.) After separation of the organic (intermediate-containing) and aqueous (bicarbonate-containing) layers, the purified hexa-acetate solution is again stripped of solvent, typically resulting as before in the formation of an oil which contains the purified intermediate.

In the event that residual acetylating agent (such as acetic anhydride) or water (from the above neutralization with sodium bicarbonate) remain in the purified hexa-acetate, an optional "azeo-drying" step may be performed. In such a step, the purified intermediate is dissolved in a suitable solvent, such as toluene, isopropanol or n-propanol. The solvent is then stripped or evaporated, along with any azeotropes formed by the solvent and the above contaminants, leaving a more highly purified hexa-acetate material.

Deacetylation (or saponification) of the purified hexa-acetate may then be performed, as for example under basic conditions such as those described in *Chem. Ber.* 56:1705 (1923) and *J. Chem. Soc.* 3166 (1960). In particular, deacetylation may be accomplished by dissolving the hexa-acetate in methanol and adding a basic catalyst selected from among lithium methoxide, sodium methoxide, barium methoxide, and potassium methoxide, sodium methoxide being preferred. (Alternatively, the catalyst may be added to the solvent before the hexa-acetate.) The amount of catalyst may range from about 0.01 to about 0.05 molar equivalents (or more, if significant amounts of acetylating agent remain). The reaction may be commenced at room temperature, resulting in the immediate precipitation of D-chiro-inositol product, and may then be continued as by heating to reflux for up to 12 hours. Upon cooling, the product may readily be isolated as by filtering and drying.

Other possible means of deacetylating the hexa-acetate include reacting the intermediate with suitable amounts of ethanol and hydrochloric acid as described in Chem. Bet. 92:173 (1959). Further deacetylation procedures which may be employed are described in H. S. Khadem, *Carbohydrate Chemistry: Monosaccharides and Their Oligomers*, Academic Press (San Diego, 1988) (cleavage of acetate esters using sodium hydroxide in acetone) and T. W. Greene and P. G. M. Wuts, *Protective Groups in Organic Synthesis*, Wiley & Sons (New York, 1991), pp. 90 and 418–420 (identifying various possible reagents and conditions).

Although the above methods result in a D-chiro-inositol product of considerable purity, it may be desired to further purify the product as by re-crystallization. In one embodiment of such a purification step, the product is dissolved in a suitable solvent such as water, after which crystallization is induced (as for example by addition of ethanol) and the solid product is collected by conventional means. Also, if decolorization of the product is desired, D-chiro-inositol can be treated with activated carbon while still in solution.

As used throughout this specification and in the appended claims, the following terms have the meanings specified:

The term "aromatic hydrocarbons" as used herein refers to cyclic, unsaturated hydrocarbons of between six and ten carbon atoms including, but not limited to, benzene, xylene and toluene.

The term "long-chain hydrocarbons" as used herein refers to straight- or branched-chain saturated hydrocarbons of between five and ten carbon atoms including, but not limited to, pentane, hexane and heptane.

The method of the present invention will be better understood in connection with the following examples, which are intended as an illustration of and not a limitation upon the scope of the invention. Both below and throughout the specification, it is intended that citations to the literature are expressly incorporated by reference.

Example 1

Preparation of hexa-O-acetyl-D-chiro-inositol from kasugamycin

In a process representative of the method of the present invention, the intermediate hexa-O-acetyl-D-chiro-inositol was prepared according to the following procedure: Kasugamycin hydrochloride (0.98 g, 2.36 mmol; Sigma Chemical Co., St. Louis) in 10 mL acetic anhydride, 10 mL acetic acid and 2 drops of concentrated sulfuric acid was heated at 100° C. under nitrogen for 24 hours. After being cooled, the brown mixture was concentrated by rotary evaporation (maximum bath temperature, 65°–70° C.) to a brown oil. This oil was diluted with 100 mL of a 1:1 mixture (by volume) of ethyl acetate and mixed hexanes and heated at reflux for 1 hour. The result was a clear, medium amber solution with brown solids. After cooling to room temperature, this mixture was filtered through a short plug (approximately 20 g) of silica gel which had been wetted with 1:1 ethyl acetate/hexanes. The silica filter material was washed with 300 mL 1:1 ethyl acetate/hexanes. The collected organic fractions were combined and concentrated by rotary evaporation to an amber oil which was found to move readily on a silica gel thin layer chromatography plate ($R_f$=0.27 using 1:1 ethyl acetate/hexanes) and could be visualized with phosphmolybdic acid after heating for 1–2 minutes. Based on the similarity of these results with data reported for hexa-O-acetyl-myo-inositol, the product was identifed as hexa-O-acetyl-D-chiro-inositol.

Example 2

Physical characterization of hexa-O-acetyl-D-chiro-inositol

Material prepared in the above manner was further purified chromatographically using silica gel and 1:1 ethyl acetate/hexanes, and concentrated to a pale amber oil. Removal of residual solvent in a vacuum oven at 65° C.

overnight gave 61% of an oil which had a $^1$H NMR spectrum consistent with that of the desired product. Because of a rotational symmetry axis, only three acetate signals are present in the proton spectrum and a relatively simple pattern of signals was observed.

$^1$H NMR (300 MHz, CDCl$_3$): δ1.99 (s,6H); 2.04 (s,6H); 2.19 (s,6H); 5.29 (dt,2H); 5.38 (d,2H); 5.42 (dd,2H).

Example 3

Preparation of hexa-O-acetyl-D-Chiro-inositol from kasugamycin

In an alternative embodiment of the method of the present invention, kasugamycin (1.00 g) in 5 mL acetic anhydride, 5 mL acetic acid and 0.26 mL concentrated sulfuric acid was heated at 100° C. under nitrogen for 24 hours. The dark brown mixture was cooled to room temperature and concentrated by rotary evaporation to an oil. This residue was slurried in 25 mL of a 3:2 mixture (by volume) of ethyl acetate and heptanes for 20 minutes, and then filtered through 2 g silica gel which had been wetted with ethyl acetate. The filter material was washed with 15 mL 3:2 ethyl acetate/hexanes, and the collected organic fractions were combined. These were then washed with saturated aqueous sodium bicarbonate (4×50 mL), water (1×50 mL) and brine (1×50 mL) and dried over sodium sulfate. The resulting material was filtered through a coarse scintered-glass funnel and concentrated to an oil by rotary evaporation.

This oil was then azeo-dried by dissolving in 20 mL toluene and reconcentrating using a rotary evaporator. The resulting 0.95 g of pale amber oil was identified the hexa-acetate intermediate by TLC.

Example 4

Conversion of hexa-O-acetyl-D-chiro-inositol to D-chiro-inositol

The hexa-acetate product of Example 3 (0.83 g) was dissolved in 10 mL of methanol. Three drops of 25% NaOMe/MeOH were added to the stirred solution which was then heated at reflux for 15 hours. The slurry was cooled to room temperature and the solids were collected by filtration. The collected solids were then washed with ambient temperature ethanol (about 5 mL) and dried to constant weight in a vacuum oven at 75° C., affording D-chiro-inositol (0.28 g, 80% yield) which by $^1$H NMR was >98% pure.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the reagents, concentrations and reaction conditions used in the method of the invention, may be made without departing from the spirit and scope thereof.

What is claimed is:

1. A method for the preparation of D-chiro-inositol from kasugamycin, comprising the steps of:
   (a) reacting kasugamycin with an acetylating agent to form a crude hexa-acetate;
   (b) purifying the crude hexa-acetate to form purified hexa-acetate;
   (c) deacetylating the purified hexa-acetate to form D-chiro-inositol; and
   (d) isolating the D-chiro-inositol.

2. A method according to claim 1 wherein the reaction in step (a) is carded out in the presence of an acid catalyst.

3. A method according to claim 2 wherein the acetylating agent is selected from the group consisting of acetic anhydride, a mixture of acetic anhydride and acetic acid, trifluoroacetic anhydride, a mixture of trifluoroacetic anhydride and trifluoroacetic acid, and a mixture of acetyl halide and acetic acid.

4. A method according to claim 3 wherein the acetylating agent is a mixture of acetic anhydride and acetic acid in a ratio of about 1:1.

5. A method according to claim 2 wherein the acid catalyst is selected from the group consisting of mineral acids and Lewis acids.

6. A method according to claim 5 wherein the mineral acid is selected from the group consisting of hydrochloric acid, hydrobromic acid, hydrofluoric acid, nitric acid, sulfuric acid, and perchloric acid.

7. A method according to claim 5 wherein the Lewis acid is selected from the group consisting of BF$_3$-etherate and FeCl$_3$.

8. A method according to claim 2 wherein the acid catalyst is selected from the group consisting of sulfuric acid and perchloric acid.

9. A method according to claim 1 wherein the purification in-step (b) comprises the sub-steps of:
   (i) substantially removing the acetylating agent to form a residue;
   (ii) diluting the residue in a suitable solvent system to form a solution of crude hexa-acetate;
   (iii) filtering the solution of crude hexa-O-acetyl-D-chiro-inositol to form a solution of purified hexa-acetate; and
   (iv) substantially removing the solvent.

10. A method according to claim 9 wherein the removal of acetylating agent in sub-step (i) is carried out by vacuum evaporation of the acetylating agent.

11. A method according to claim 9 wherein the solvent system in sub-step (ii) comprises a first, polar solvent is selected from the group consisting of ethyl acetate, CH$_3$CN, CH$_2$Cl$_2$, CHCl$_3$, and 1,2-dichloroethane.

12. A method according to claim 11 wherein the solvent system additionally comprises a second, non-polar solvent selected from the group consisting of long-chain hydrocarbons and aromatic hydrocarbons.

13. A method according to claim 11 wherein the second, non-polar solvent is selected from the group consisting of pentane, hexane, heptane, benzene, xylene, and toluene.

14. A method according to claim 13 wherein the solvent system is a mixture of ethyl acetate and hexane in a ratio of about 1:1.

15. A method according to claim 9 wherein the filtering in sub-step (iii) comprises passing the solution of crude hexa-acetate through a filter material selected from the group consisting of silica gel, alumina, activated carbon, diatomaceous earth, and a mixture of alumina and diatomaceous earth.

16. A method according to claim 15 wherein the filter material is silica gel.

17. A method according to claim 9 comprising the additional sub-step, between sub-steps (ii) and (iii), of neutralizing the solution of crude hexa-acetate.

18. A method according to claim 17 wherein the neutralization is carded out by washing the solution of crude hexa-acetate with a solution of sodium carbonate.

19. A method according to claim 9 comprising the additional sub-step, between sub-steps (iii) and (iv), of neutralizing the solution of purified hexa-acetate.

20. A method according to claim 19 wherein the neutralization is carded out by washing the solution of purified hexa-acetate with a solution of sodium carbonate.

21. A method according to claim 9 comprising the additional sub-step, after sub-step (iv), of azeo-drying the purified hexa-acetate.

22. A method according to claim 21 wherein the azeo-drying is carried out using a solvent selected from the group consisting of toluene, isopropanol and n-propanol.

23. A method according to claim 1 wherein the deacetylation in step (c) is carried out by dissolving the hexa-acetate in a solvent selected from the group consisting of methanol and ethanol and adding a sufficient amount of a basic catalyst selected from the group consisting of lithium methoxide, sodium methoxide, barium methoxide, and potassium methoxide to produce deacetylation.

24. A method according to claim 23 wherein the catalyst is sodium methoxide.

25. A method according to claim 1 wherein the deacetylation in step (c) is carried out by reacting the hexa-acetate with suitable amounts of ethanol and hydrochloric acid.

26. A method according to claim 1 comprising the additional step, after the isolation in step (d), of purifying the D-chiro-inositol by re-crystallization.

27. A method according to claim 26 wherein the re-crystallization of D-chiro-inositol comprises the sub-steps of:

(i) dissolving the D-chiro-inositol in water; and
(ii) precipitating the D-chiro-inositol from solution.

* * * * *

UNITED STATES PATENT AND TRADEMARK OFFICE
CERTIFICATE OF CORRECTION

PATENT NO. : 5,463,142
DATED : October 31, 1995
INVENTOR(S) : David A. Riley, Steven A. Chamberlin and Ashok V. Bhatia It is certified that error appears in the above-indentified patent and that said Letters Patent is hereby corrected as shown below:

In column 1, line 49 delete "carded" and insert -- carried--.

In column 1, line 62 delete "carded" and insert --carried--.

In column 2, line 59 delete "carded" and insert --carried--.

In column 4, line 56 delete "phosphmolybdic" and insert -- phosphomolybdic--.

In column 6, line 3 delete "carded" and insert --carried--.

In column 6, line 64 delete "carded" and insert --carried--.

In column 7, line 3 delete "carded" and insert --carried--.

Signed and Sealed this

Thirteenth Day of August, 1996

Attest:

BRUCE LEHMAN

Attesting Officer

Commissioner of Patents and Trademarks